United States Patent [19]

Ausich et al.

[11] Patent Number: 5,858,700

[45] Date of Patent: *Jan. 12, 1999

[54] PROCESS FOR THE ISOLATION AND PURIFICATION OF LYCOPENE CRYSTALS

[75] Inventors: Rodney L. Ausich; David J. Sanders, both of Des Moines, Iowa

[73] Assignee: Kemin Foods, LC, Des Moines, Iowa

[*] Notice: The term of this patent shall not extend beyond the expiration date of Pat. No. 5,648,564.

[21] Appl. No.: 832,282

[22] Filed: Apr. 3, 1997

[51] Int. Cl.$^6$ .............................. C12P 23/00; C12N 1/00
[52] U.S. Cl. ........................... 435/67; 435/166; 435/257; 435/822; 435/911; 435/946
[58] Field of Search ..................... 424/195.1; 514/762; 435/67, 166, 257, 822, 911, 946

[56] References Cited

U.S. PATENT DOCUMENTS

| | | | |
|---|---|---|---|
| 2,842,599 | 7/1958 | Isler et al. | 260/601 |
| 3,097,146 | 7/1963 | Swarthout et al. | 195/78 |
| 3,369,974 | 2/1968 | Ninet et al. | 195/28 |
| 3,467,579 | 9/1969 | Bianchi et al. | 195/28 |
| 3,998,753 | 12/1976 | Antoshkiw et al. | 252/312 |
| 4,105,855 | 8/1978 | Schulz et al. | 560/190 |
| 5,019,405 | 5/1991 | Sapers | 426/250 |
| 5,166,445 | 11/1992 | Meyer | 568/2 |
| 5,208,381 | 5/1993 | Meyer | 568/10 |
| 5,245,095 | 9/1993 | Graves et al. | 585/351 |
| 5,304,478 | 4/1994 | Bird et al. | 435/172.3 |
| 5,429,939 | 7/1995 | Misawa et al. | 435/67 |
| 5,530,188 | 6/1996 | Ausich et al. | 800/205 |
| 5,530,189 | 6/1996 | Ausich et al. | 800/205 |
| 5,648,564 | 7/1997 | Ausich et al. | 568/834 |

FOREIGN PATENT DOCUMENTS

| | | |
|---|---|---|
| 0 608 027 A2 | 1/1994 | European Pat. Off. . |
| 7147929 | 6/1995 | Japan . |
| 595444 | 2/1978 | Switzerland . |
| 2274235 | 7/1994 | United Kingdom . |
| WO 95/16363 | 6/1995 | WIPO . |
| WO 96/13149 | 5/1996 | WIPO . |
| WO 96/13178 | 5/1996 | WIPO . |

OTHER PUBLICATIONS

Giovannucci et al., *J. Natl. Cancer Inst.*, 87(23): 1767–1776 (Dec. 6, 1995).
Morris et al., *J. Amer. Med. Assoc.*, 272(18): 1439–1441 (1994).
*Official Methods of Analysis of AOAC International*, 16$^{th}$ ed., vol. 1, P. Cunniff, ed., AOAC International (Gaithersburg,, MD: 1996).
Horsch et al., *Science*, 227:1229–1231 (1985).
Corrick et al., *Gene*, 53:63–71 (1987).
Hamer and Timberlake, *Mol. Cell. Biol.*, 7:2352–2359 (1987).
Perry et al., *J. Bacteriol.*, 168:607 (1986).

*Primary Examiner*—David M. Naff
*Assistant Examiner*—Janet M. Kerr
*Attorney, Agent, or Firm*—Welsh & Katz, Ltd.

[57] ABSTRACT

A process for isolating and purifying lycopene crystals from a biological lycopene source is disclosed. A lycopene-containing oleoresin is saponified in a composition of propylene glycol and aqueous alkali to form lycopene crystals. Crystallization is achieved without the use of added organic solvents. The crystals are isolated and purified. The substantially pure lycopene crystals so obtained are suitable for human consumption and can be used as a nutritional supplement and as an additive in food.

19 Claims, No Drawings

PROCESS FOR THE ISOLATION AND PURIFICATION OF LYCOPENE CRYSTALS

DESCRIPTION

1. Technical Field

The present invention relates to a process for isolating and purifying lycopene, and more particularly to a process for isolating and purifying lycopene from a biological source in a crystalline form suitable for human consumption.

2. Background Of The Invention

Carotenoids include hydrocarbons (carotenes) and their oxygenated, alcoholic, derivatives (xanthophylls). Representative examples of carotenes include beta-carotene, alpha-carotene, and lycopene. Representative examples of xanthophylls include lutein, zeaxanthin, capsorubin, capsanthin, astaxanthin, and canthaxanthin.

Carotenoids are abundant in fruits and vegetables and have been studied extensively as antioxidants for the prevention of cancer and other human diseases. Among the dietary carotenoids, the focus has been on beta-carotene that has been established to play an important role in the prevention of various types of cancer. More recent research has shown that other carotenoids, including lycopene, possess strong antioxidant capabilities and can be useful in the prevention of diseases including cancer. See, e.g. European Patent No. 600544 or Canadian Patent No. 2,109,750. For example, it has been reported that the consumption of lycopene leads to a reduced risk of prostate cancer. See, e.g. Giovannucci et al., *J. Natl. Cancer Inst.* 87(23):1767–1776 (Dec. 6, 1995). It has also been reported that an increased level of serum carotenoids other than beta-carotene is associated with a lower incidence of heart disease [Morris et al., 1994, *J. Amer. Med. Assoc.* 272(18): 1439–1441]. The carotenes, because of their yellow to red coloration and natural occurrence in human foods, also find uses as food colorants See, e.g. U.S. Pat. No. 5,019,405 or 3,998,753. Lycopene is also known as $\psi,\psi$-carotene. Lycopene can be used as a nutritional supplement and food additive.

Although present in many plant tissues, carotenoids free of other plant pigments are most readily obtained from lycopene-accumulating fruits such as tomatoes and watermelon. U.S. Pat. Nos. 3,097,146 and 3,369,974 describe the production of lycopene by fermentation of the fungus *Blakeslea trispora*, from which the lycopene is purified by extraction with hexane and chromatographed on alumina.

The hydrocarbon carotenes, such as lycopene, are typically present in uncombined, free form entrapped within chromoplast bodies within plant cells. In contrast, xanthophylls are typically present in plant chromoplasts as long chain fatty esters, typically diesters, of acids such as palmitic and myristic acids.

Although chemical processes for the synthesis of lycopene from commercially available starting materials are known, such processes are extremely time-consuming, involve multiple steps, and have not provided an economical process for the production of substantially pure lycopene suitable for human consumption or cosmetic use. See, e.g. U.S. Pat. Nos. 2,842,599, 4,105,855, 5,166,445 or 5,208,381. For example, U.S. Pat. No. 2,842,599 describes the synthesis of lycopene by condensing 2,6,11,15-tetramethyl-2,4,6,8,10,12,14-hexadecaheptaene-1,16-dial with triphenyl-(3,7-dimethyl-2,6-octadien-1-ylidene)-phosphine and U.S. Pat. No. 4,105,855 describes the synthesis of lycopene by dimerizing 3,7,11,15-tetramethylhexadeca-2,4,6,8,10,14-hexaen-1-yl-triphenylphosphonium bisulfate.

One alternative for providing a form of lycopene suitable for consumption (comestible) or cosmetic use is to stop short of purifying lycopene from an edible lycopene-producing biological source, and use a crude lycopene preparation. U.S. Pat. No. 5,245,095 describes the precipitation of carotenoids from the liquid fraction of homogenized vegetables with a calcium-containing precipitation agent. PCT WO 95/16363, published Jun. 22, 1995, describes the fractionation of a tomato into several useful fractions, including a tomato pulp oleoresin. European Patent Application No. EP 608027A2 describes an edible crude lycopene preparation resulting from the isolation of lycopene-containing chloroplasts from tomato. Another crude lycopene preparation suitable for consumption is described in British Patent Application No. GB 2274235 disclosing the use of lycopene-containing vegetable powder in edible oils.

The disadvantage of this approach is that the comestible lycopene is in impure form, albeit processed relative to a tomato source.

One process for the large-scale production of substantially pure lycopene is a process that extracts, isolates and purifies lycopene from natural sources. However, previous methods that isolate lycopene from plants use a number of organic solvents in the last phase of recovery.

The disadvantage of these methods is that the carotenes can retain some of the solvent(s) from which they are isolated and purified (recovered). In addition, these methods often require the washing of the carotenes with more solvents. The solvents can be usually removed by drying the crystals at elevated temperatures. As shown in Example 7, lycopene can degrade under such conditions. But in some instances, the solvent is difficult or impossible to remove. Traces of toxic organic solvents in the isolated, purified carotene product make it unsuitable for human consumption. Another disadvantage of the use of a process that employs organic solvents is that such solvents can be difficult to handle and can present physical and chemical hazards. Still another disadvantage of that use is that organic solvents are a hazardous waste and present a disposal problem.

PCT WO 96/13178, published May 9, 1996, describes the preparation of stable crystalline lycopene concentrates by size-reducing lycopene crystals in a food-compatible liquid medium that essentially does not dissolve lycopene, such as propylene glycol, ethanol, or glycerol. The lycopene crystals of that disclosure were first obtained by extraction of a lycopene-containing oleoresin with an ethyl acetate and acetone solvent to provide lycopene crystals having a size of 15–120 $\mu$m that were ground to a size of 1–3 $\mu$m in the liquid medium.

Genetic engineering has made it possible to convert a wide variety of biological hosts into lycopene sources. It is desirable to obtain edible or comestible lycopene from these biological sources while eliminating the need to ingest the biological source. An advantage to using an alternative biological source to, for example, tomatoes, is that use of an alternative reduces waste of a potential food.

There is therefore a need for an economical means of production of edible or comestible, substantially pure lycopene from a wide variety of biological sources in which the use of toxic or hazardous organic solvents is minimized.

BRIEF SUMMARY OF THE INVENTION

The present invention relates to a process for isolating and purifying lycopene from a lycopene-containing biological source. The biological sources preferably are known to contain high concentrations of lycopene, such as tomatoes or cells genetically engineered to accumulate lycopene.

A contemplated process uses a lycopene-containing biological source cell extract (oleoresin) that is substantially free of organic solvent; i.e., the oleoresin contains about 0.1–1 percent organic solvent. Preferably, the oleoresin is a food-grade plant extract. The oleoresin contains cell debris that typically contains di- and triglycerides and phosphonates that solubilize and entrap the lycopene. The extract is admixed with a composition containing propylene glycol, water and an alkali, preferably potassium hydroxide, to form a saponification reaction mixture of which oleoresin and propylene glycol together constitute at least about 50 weight percent.

The saponification reaction mixture so formed is maintained at a temperature of about 50° C. to about 80° C. for a time period (typically at least 0.5 hours) sufficient to saponify the cell debris such as di- and triglycerides and phosphonates and form a saponified reaction mixture that contains lycopene crystals and water-dispersible saponification products. The term water-dispersable is intended herein to include water-soluble.

The saponified extract is admixed with a diluting amount of water to disperse the water-dispersible saponification products (impurities), and to reduce the viscosity of the reaction mixture. The diluted admixture is gently admixed until homogeneous and then filtered to collect the lycopene crystals. The collected lycopene crystals are washed with water (preferably warm), and dried. No organic solvent other than propylene glycol is used in the last phase of isolation and purification (recovery) of the lycopene from the lycopene-containing oleoresin.

The present invention has several advantages. One advantage of this invention is that it provides a process for producing a substantially pure lycopene that is suitable for human consumption without the use of relatively toxic organic solvents during the last phase of isolation or crystallization. Another advantage is that the contemplated invention provides a process for producing a comestible, substantially pure lycopene without the need for recrystallization. Yet another advantage of this invention is that it provides a process for producing a substantially pure lycopene that is economical and easy to perform on a large commercial scale. A further advantage of this invention is that it provides a process for producing substantially pure lycopene from a wide variety of biological sources, including genetically engineered biological sources. Still further advantages will be apparent to a worker of ordinary skill from the description that follows.

DETAILED DESCRIPTION OF THE INVENTION

According to the present invention, lycopene is isolated and purified from a lycopene-containing biological source, preferably a plant known to contain high concentrations of the desired lycopene or a biological source that has been genetically-engineered to accumulate lycopene.

Allowed, co-assigned U.S. application Ser. No. 08/576,778, whose disclosures are incorporated herein by reference, discloses a process for the formation, isolation and purification of comestible xanthophyll crystals from plants. Briefly, the xanthophyll crystal isolation and purification process uses a xanthophyll ester-containing food grade plant extract (oleoresin) as a starting material. The xanthophyll ester-containing extract is admixed with a composition containing propylene glycol (also known as 1,2-propanediol), water and an alkali to form a saponification reaction mixture. The saponification reaction mixture so formed is maintained at a temperature of about 65° C. to about 80° C. for a time period sufficient to saponify the cellular debris and form a saponified reaction mixture that contains free xanthophyll in the form of crystals. The saponified extract is admixed with a diluting amount of water to dissolve the water-soluble impurities and reduce the viscosity of the reaction mixture. The diluted admixture is gently admixed until homogeneous and then filtered to collect the comestible xanthophyll crystals.

Surprisingly, although lycopene is typically present in uncombined, free form within plant and other cells, rather than as an ester that would call for saponification, the xanthophyll saponification/crystallization reaction described before can be adapted to isolate and purify comestible lycopene crystals from a plant-derived oleoresin. It is likewise surprising that that saponification/crystallization reaction can be adapted to isolate and purify comestible lycopene crystals from a lycopene-containing oleoresin obtained from cells of biological sources other than plants.

In the case of xanthophyll, the saponification step serves to convert the xanthophyll from the ester form to the free form, which then crystallizes. In the case of lycopene, the saponification step serves to convert lycopene-entrapping cellular debris such as di- and triglycerides and phosphonates present in the extract to their free forms, which causes the lycopene to form comestible crystals. The process disclosed hereinafter provides such an isolation and purification of comestible lycopene crystals suitable for consumption or cosmetic use.

As a practical matter, the process of forming a saponification reaction mixture to isolate and purify xanthophyll crystals can involve more steps than the process of forming a saponification reaction mixture to isolate and purify lycopene crystals. Xanthophyll-containing oleoresin, such as marigold oleoresin, is a solid at ambient temperature (about 20° C.), whereas lycopene-containing oleoresin such as tomato oleoresin can have more fluid character. As a result, a homogenous saponification reaction mixture for producing xanthophyll is formed from marigold oleoresin by first heating a marigold oleoresin and propylene glycol admixture to 50°–60° C., before adding alkali and water to complete the saponification reaction mixture, whereas the saponification reaction mixture components utilized here can be admixed in any order to isolate and purify lycopene from tomato oleoresin. It is preferred, however, that the oleoresin be first admixed with propylene glycol to form a homogeneous admixture, after which the water and alkali are added.

Tomatoes are an excellent source of lycopene because they contain one of the highest known concentrations of lycopene in nature, about 0.01 weight percent lycopene on a dry weight basis. Other plants that are known to contain high concentrations of lycopene can also be utilized. Other plant sources of lycopene include fruits such as Ruby Red or Redblush grapefruit, watermelon, and persimmons such as the Fuyu and Honan Red varieties.

Other biological sources of lycopene include bacteria, fungi or mammalian cells that are genetically engineered to produce lycopene. Several patents disclose DNA and methods for production of carotenoids in various biological sources. See. e.g. U.S. Pat. Nos. 5,530,189; 5,530,188; 5,429,939; 5,304,478; 3,467,579; and Swiss Patent No. 595444.

For example, U.S. Pat. No. 5,530,189, the disclosures of which are incorporated herein by reference, discloses the production of lycopene in bacteria, yeast, fungi and higher plants. In that patent, DNA from *Erwinia herbicola* (now known as *Escherichia herbicola*) is introduced into the biological organism providing the enzymes needed to convert ubiquitous cellular precursors into lycopene that is accumulated; or by disabling enzymes that convert produced lycopene to another product such as beta-carotene, that otherwise prevents lycopene from accumulating; or by providing additional enzymes to produce lycopene, allowing lycopene to accumulate in spite of the action of enzymes that convert lycopene to another material.

The biosynthetic path to and from lycopene is disclosed in that patent. Briefly, ubiquitous precursors are converted into phytoene by the action of geranylgeranyl pyrophosphate synthase (GGPP synthase) and phytoene synthase. The phytoene is thereafter converted into lycopene by the action of an enzyme referred to as phytoene dehydrogenase-4H.

As taught in WO 96/13149 (published May 9, 1996), for a host that usually accumulates lycopene, only a gene for phytoene synthase need be introduced to cause enhanced lycopene biosynthesis and accumulation. For a host that does not usually accumulate lycopene, lycopene can be produced from ubiquitous precursors by introducing the structural genes for the three enzymes, GGPP synthase, phytoene synthase, and phytoene dehydrogenase-4H.

Plasmids containing DNA encoding those three enzymes have been deposited with the American Type Culture Collection (ATCC) 12301 Parklawn Drive, Rockville, Md., 20852. Those plasmid designations are listed below, and are followed by their ATCC accession numbers in parentheses. Plasmids that together encode the full, biologically active GGPP synthase and phytoene synthase proteins are pARC417BH (40755), pARC489B (40758), pARC489D (40757), pARC285 (40756), pARC140N (40753). Plasmids that each encode a full, biologically active phytoene dehydrogenase-4H protein are pARC496A (40803), pARC146D (40801), pATC228 (40802), pATC1616 (40806).

U.S. Pat. No. 5,530,189 also discloses examples of lycopene production in a variety of cells: *Eschericia coli, Rhodobacter sphaeroides, R. rubrum, Aspergillus nidulans, Saccharomyces cerevisiae, Pichia pastoris, Agrobacterium tumefaciens,* tobacco and alfalfa. That patent demonstrates that other bacteria, yeast, fungi, and higher plants can be made to produce lycopene. Plasmid constructs can be made using the genes disclosed in that patent for virtually any plant or unicellular host system using techniques well known in the art.

In addition, DNA from other sources encoding GGPP synthase, phytoene synthase and phytoene dehydrogenase can be used to produce such plasmid constructs, as reported in U.S. Pat. No. 5,429,939 [European Patent Application 0 393 690 A1, published Apr. 20, 1990] for DNA from *Erwinia uredovora* 20D3 (ATCC 19321). Examples 10–13 herein describe the application of the lycopene purification process of the invention to those genetically-engineered biological sources.

A contemplated source contains lycopene along with cellular debris such as proteins, di- and triglycerides and phosphonates such as lecithins, cephalins and inositides that are esters of a $C_{12}$–$C_{18}$ long chain fatty acid such as lauric, myristic, oleic, linolenic and palmitic acids. Lycopene is present as the free hydrocarbon, having no substituent groups, entrapped by the cellular debris.

The lycopene is extracted from the biological source, preferably from genetically-engineered cells or the fruits or fruit portions such as skins, with an appropriate organic solvent or a mixture of solvents that are themselves readily removable from the extract. When fruit is utilized, it is preferably ripe. The use of fruits or fruit portions as a source of lycopene avoids difficulty in the separation of the lycopene from other pigments such as chlorophyll that can be present in other plant portions, but is usually absent from ripe fruit. The use of genetically-engineered bacteria, yeast or fungal cells can also avoid this problem.

In one preferred embodiment of the invention, tomatoes are used as a source of lycopene. Several forms of tomato can be used including tomato skins, tomato paste and tomato pomace. Tomato pomace is a commercially available feed ingredient made from dried tomato skins, seeds and other tomato by-products.

In another preferred embodiment of the invention, genetically-engineered cells are used as a source of lycopene. Several forms of genetically engineered cells can be used, including yeast, fungi, bacteria, higher plants and cultured mammalian cells.

In one illustrative embodiment of the invention, lycopene is extracted from tomato skins with hexanes. The extraction is carried out according to procedures known in the art for preparing an oleoresin, and other organic solvents can be used, but hexanes are preferred and are used illustratively herein. The solvent is removed, resulting in an extract that contains a high level of the lycopene and is about 99 percent and preferably about 99.9 percent free of the extracting organic solvent; i.e., contains less than about 1 percent and preferably less than about 0.1 percent organic solvent by weight.

Such a resulting solvent-free pigment-containing extract is referred to in the art as an oleoresin. An oleoresin contemplated here contains previously discussed cellular debris such as di- and triglycerides and phosphonates in addition to the lycopene. An oleoresin contemplated here is lycopene-containing cellular extract from any of the biological sources contemplated.

Cellular extracts or oleoresins of the lycopene-containing biological source are preferred for use in a process of the invention. Extraction with an organic solvent prior to the saponification step serves to inactivate many enzymes, and also to remove some organic impurities before the entrapped organic-soluble lycopene is released by the saponification/crystallization reaction. Direct saponification of the biological source still frees the entrapped lycopene, but the lycopene crystal yield is reduced as a result of the increased cellular organic impurities.

A wide variety of factors affect the extraction efficiency of lycopene from the biological source. These factors include the drying conditions of the biological lycopene source, and the presence of additives such as antioxidants or vegetable oil, such as corn oil or canola oil, as are shown in Examples 1, 2, 5 and 6.

Organic solvents that have been used to initially extract carotenoids from biological sources to form an oleoresin include methanol, acetone, ethyl acetate, diethyl ether, petroleum ether, hexanes, heptanes, chloroform, and tetrahydrofuran. Other solvents can be used, such as hexane, dichlormethane, butyl acetate, ethanol, methyl acetate, propane and their mixtures as stated in PCT WO 95/16363, published Jun. 22, 1995.

In the present invention, the oleoresin is saponified by admixture with propylene glycol (1,2-propanediol), water and an alkali such as sodium, potassium, calcium, magnesium or ammonium hydroxide or trisodium phosphate. The saponification reaction admixture components (oleoresin, propylene glycol, alkali and water) can be combined in any order, as noted before. For example, the propylene glycol can be admixed with the oleoresin first, and the water and alkali solution blended therewith, or the propylene glycol can be admixed last. In preferred practice, the water and alkali are thoroughly mixed separately to form an aqueous alkali solution. It is also preferred to blend the oleoresin with propylene glycol while warming to form a homogeneous mixture. In particularly preferred practice, an aqueous alkali solution is slowly added to a homogeneous mixture of oleoresin and propylene glycol to form a complete saponification reaction mixture.

The lycopene is present in the aqueous propylene glycol-containing saponified oleoresin as crystals of lycopene that are clearly visible under a microscope in most instances. In addition, the saponification reaction forms water-dispersible products including fatty acid soaps and glycerin that liberate the lycopene. Thus, crystallization of the lycopene is achieved by the saponification reaction and not by the addition of various organic solvents as has been done previously.

Propylene glycol is used in a process of the invention instead of more toxic alternatives. Exemplary toxicities of propylene glycol and several solvents previously used for lycopene crystal recovery are available from several sources. Comparative oral toxicities in the rat from *The Merck Index,* 11th ed., Merck & Co., Inc., Rahway, N.J. (1989) are provided in the Table below as $LD_{50}$ values.

| Reported Rat Toxicities | |
|---|---|
| Solvent | $LD_{50}$ (mL/kg) |
| Propylene Glycol | 25 |
| Ethyl Acetate | 11.3 |
| Acetone | 10.7 |
| Ethyl Alcohol | 10.6–7.6 |
| Chloroform | 2.18 |
| Pyridine | 1.58 |

Large crystal size is important to obtaining lycopene at the purity desired. To obtain the desired large crystals (average size about 0.01 to about 0.5 mm), the concentrations of the four constituents of the saponification reaction mixture are preferably present at about 25 to about 50 weight percent lycopene-containing oleoresin, about 25 to about 60 weight percent propylene glycol, about 5 to about 20 weight percent alkali such as potassium hydroxide, and about 5 to about 25 weight percent water, as initially admixed components; i.e., components before reaction or admixture to form the saponification reaction mixture. The oleoresin and propylene glycol together constitute at least about 50 weight percent of the saponification reaction mixture, and preferably together constitute about 80 weight percent of the saponification reaction mixture.

Preferably, potassium hydroxide is used as the alkali, in the form of a solution of 45 percent caustic potash, so a preferred weight ratio is about 4–5:3–4:1:1 oleoresin to propylene glycol to alkali (measured as the weight of potassium hydroxide) to water. When an alkali of a molecular weight different from that of potassium hydroxide is used, the weight ratio is adjusted accordingly. Thus, the phrase "as potassium hydroxide" is utilized to express the fact that the weight ratio uses potassium hydroxide as a basis for calculation.

In a particularly preferred embodiment, those weights are about 50 percent oleoresin, about 30 percent propylene glycol, about 10 percent potassium hydroxide, and about 10 percent water, as exemplified in Example 1.

These ratios can vary widely and still successfully lead to comestible lycopene crystals.

In addition, the saponification reaction preferably proceeds slowly. In an exemplary embodiment, about 6 g of freeze-dried tomato skin extract is mixed with the propylene glycol, which finely disperses in the extract. The mixture is heated to a temperature of about 50° to about 60° C., preferably about 55° C., to obtain a homogenous liquid having a viscosity similar to that of motor oil at room temperature. An aqueous potassium hydroxide solution is added slowly and evenly to the dispersed extract (oleoresin) over a period of time to form the saponification reaction mixture. At least 1 minute, but preferably 30 minutes are used for saponification reaction mixture formation with the above component amounts, and the mixture is maintained with gentle agitation for a period of time sufficient to saponify the cellular debris (e.g. di- and triglycerides and phosphonates) present, at least 0.5 hours, but preferably 2 hours.

When the alkali solution is initially added to the oleoresin, the temperature rises to about 70° C. and additional heat is added to maintain the temperature at about 50° C. to about 80° C., and preferably of about 65° C. during the entire reaction; i.e., to saponify the cellular debris such as di- and triglycerides and phosphonates. Saponification can be readily determined by thin layer chromatography (TLC) or by observing the alteration of the blending characteristics of the mixture in that the saponified reaction mixture is less viscous than the unreacted composition.

Sodium hydroxide or another alkali can also be employed for the saponification, but the formed potassium soaps are more desirable because they are generally more dispersible in aqueous solutions than are sodium soaps, and ammonium soaps tend to lose ammonia at elevated temperatures. The alkali used in the preferred embodiment of the invention is preferably an aqueous alkaline potash solution that is 45 weight percent potassium hydroxide (45 percent caustic potash).

The saponification reaction cleaves proteins present in the cellular debris as well as the fatty acids from the di- and triglycerides and phosphonates, decreasing the solubility of the lycopene in the resulting medium so that crystals form. It is possible that propylene glycol mono-fatty acid esters are formed during the saponification. If present, those materials do not interfere with crystallization of the lycopene, possibly because of their greater water solubility as compared to proteins, di- or triglyceride esters of those fatty acids.

The saponified reaction mixture so formed is then diluted by admixture with low ionic strength (deionized) water, preferably warm, e.g. about 40°–80° C., to further reduce the viscosity of the reaction mixture and to disperse water-dispersible impurities; e.g., the soaps and glycerin. If cold water is used, additional heat is provided to the diluted reaction mixture to maintain a temperature range of about 40° C. to about 80° C., preferably about 70° C.

If the temperature is too cold, the diluted reaction mixture can become too viscous to filter. If the temperature is too hot, the diluted reaction mixture can foam, which interferes with crystal recovery.

Sufficient water is added to form a diluted reaction mixture that contains about 5 to about 25 weight percent of the original saponification reaction mixture in the final total weight. Thus, about 3 to about 19 parts by weight of diluting water are added per reaction mixture part by weight. For a preferred embodiment, the ratio is about 20 weight percent initial saponification reaction mixture to about 80 weight percent diluting water (4 parts by weight).

The diluted reaction mixture formed by addition of water is gently agitated until homogeneous and then either pumped or otherwise fed into a filtration device that collects the crystals. Virtually any filtration device known in the art can be used. In a preferred embodiment of the invention, the mixture is fed into a centrifuge basket filter having a 8–400 μm maximum pore size. As is well known, the larger pore sizes have fewer problems with clogging of the filter.

The majority of the chemical impurities in the extract (compounds other than lycopene) are removed during the filtration step due to the dispersible nature of the hydrolyzed proteins and fatty acid soaps formed during saponification and their solubilizing power in a largely aqueous composition, and the insoluble nature of the lycopene crystals in that same aqueous composition. Other water-soluble impurities such as glycerin, anthocyanins, hydrolyzed proteins, oligosaccharides and water-soluble flavonoids that can also be present in the saponification reaction mixture are also removed.

After filtration, the collected crystals are washed extensively with low ionic strength (deionized) water at a temperature range of about 70° C. to about 90° C., preferably about 85° C. At the warm temperature employed, the water removes most of the residual chemical contaminants that may be present such as the potassium or sodium hydroxide, residual soap, the propylene glycol and the like that are used and form in the saponification reaction.

The washed crystals are dried by a suitable methods such as freeze drying, rotary vacuum drying or by purging with heated nitrogen. The use of heated nitrogen instead of warm air minimizes the oxidative degradation of the lycopene.

Based on UV/visible spectrophotometry, the resulting crystals obtained by this process contain approximately 65 to 85 percent of the total carotenoids present in the lycopene-containing oleoresin, and are deemed substantially pure lycopene. In an exemplary embodiment of the invention in which lycopene is isolated from tomato skin extract, the carotenoids, as determined by HPLC analysis, comprises about 75 to 95 percent lycopene and traces of other carotenoids such as beta-carotene and xanthophylls. The presence of low levels of these other carotenoids is not of any concern because those other carotenoids are frequently used dietary supplements and are found routinely in human serum or plasma.

The lycopene crystals contain water, and can contain traces of fatty acid soaps and/or fatty acids not completely washed from the crystals. However, the substantially pure lycopene obtained from this process does not contain residues of toxic organic solvents, (i.e., solvents other than propylene glycol) or other toxic compounds, and is suitable for human consumption.

The dried lycopene crystals so formed are typically admixed with a triglyceride oil such as an edible or cosmetically acceptable oil to form a lycopene crystal suspension or solution for use in foods or as a cosmetic colorant. The lycopene content of the admixture is typically about 0.1 to about 35 percent by weight. Exemplary edible and cosmetically acceptable oils include candelilia, coconut, cod liver, cotton seed, menhaden, olive, palm, corn, soybean, peanut, poppy seed, safflower and sunflower oil. The use of an oil having a relatively high concentration of unsaturated fatty acids is preferred; i.e., the use of an oil having an iodine value of about 100–150 is preferred. The admixture is typically carried out using a high shear mixing apparatus, as is well known. Co-solvents and additives such as the comestible solvent ethanol and the natural-product antioxidant α-tocopherol, respectively, can also be present.

The following examples are offered to illustrate but not limit the present invention.

BEST MODE FOR CARRYING OUT THE INVENTION

EXAMPLE 1

Isolation of Lycopene From Tomato Skins

Extraction

Wet tomato skins (8 kg of 50 lbs) from Siagra Co., Chengmai, Thailand, were freeze-dried. Corn oil was added to the freeze-dried tomato skins (2.08 kg) to five weight percent corn oil relative to the weight of the freeze-dried tomato skins.

The mixture was ground in a WILEY™ pellet mill (Fisher Scientific, Pittsburgh Pa.) to an average particle size of less than two millimeters in diameter, then pelleted in a laboratory pellet mill (California Pellet Mill Co., San Francisco Calif.) fitted with a ⅛" die. The temperature of the pellets coming out of the mill was 58° to 60° C. The pellet size ranged from ⅛" to ¼" in length. The pellets were of fair durability. The pellets were allowed to cool to room temperature and then stored frozen until extraction.

Lycopene concentration can be conveniently determined by a modification of the Association of Official Analytical Chemists (AOAC) method for carotenes, *Official Methods of Analysis of AOAC International*, 16th Ed., Vol. 1, P. Cunniff, ed., AOAC International (Gaithersburg, Md.: 1996), March Supplement, Sects. 45.1.03–04.

Briefly, the AOAC method is to homogenize a blanched carotenoid source (2–5 g boiled 5–10 minutes in water); extract the homogenate in the blender with 40:60 acetone-:hexane (100 mL) containing magnesium carbonate ($MgCO_3$, 0.1 g); wash the residue with acetone (2×25 mL), then hexane (1×25 mL), combining the extracts; remove the acetone from the extracts by washing with water (5×100 mL); then diluting to volume with hexane and acetone (9 mL acetone, 100 mL total volume) to determine the carotenoid content spectrophotometrically.

A modification of the AOAC method to conveniently determine the lycopene concentration is to dilute to volume with hexanes only after the acetone is washed out with water or to extract only with hexanes. The spectrum of lycopene in hexanes is reported in the published literature, with maxima in hexanes at 446–448 nm, 474–475 nm, and 505–506 nm. Liaaen-Jensen, *Phytochemistry*, 4:925–931 (1965); Reichenbach and Kleinig, *Arch. Mikrobiol.*, 76:364–380 (1971). The carotenoid concentration is conveniently determined using the extinction coefficient of 3450 at 472 nm. Liaaen-Jensen, *Phytochemistry*, 4:925–931 (1965); Reichenbach and Kleinig, *Arch. Mikrobiol.*, 76:364–380 (1971).

For extraction, the dried tomato skin pellets were divided into two 4 L separatory funnels, soaked in hexanes at 38° to 41° C. for thirty minutes, and drained. This procedure was repeated 6 to 7 times to ensure complete extraction of the pigment present in the tomato skins.

High performance liquid chromatography (HPLC) of the hexanes extracts of the tomato skins showed that the great majority of the extracts (about 90 percent) was lycopene, and the remainder was beta-carotene, xanthophylls, and unidentified compounds. The HPLC reverse phase analysis method was adapted from Khachik, *Pure and Applied Chemistry,* 63(1):71–80 (1991). The amount of lycopene and beta-carotene decreased with each subsequent wash, whereas the amount of unidentified compounds remained essentially the same at about 1 percent of the extracted compounds.

The first four hexanes extracts were combined for each of the two sets of pellets (both from the same samples), and the hexanes were evaporated in each case using vacuum and heat. After the hexanes had been removed, oily extracts (124 g and 153 g) remained (lycopene-containing oleoresins), which contained pigment (3.55 g pigment/kg oleoresin and 3.43 g pigment/kg oleoresin, respectively). Small crystals of lycopene were observed in the extracts.

Saponification/Crystallization Reaction

The lycopene-containing tomato skin oleoresin from the first extraction was saponified as follows. With stirring in a 500 mL beaker, propylene glycol (67.4 g; 29 weight percent of the final reaction mixture weight ratio 3.3) was added to the lycopene-containing oleoresin (114 g; 50 weight percent of the final reaction mixture weight ratio 5.5), and the mixture was heated to 55° C. in a water bath.

The saponification reaction mixture was completed by addition of an aqueous alkaline potash solution containing 45 weight percent potassium hydroxide (45.9 g of 45 percent caustic potash solution; 9 weight percent of the final reaction mixture KOH, weight ratio 1; 12 weight percent of the final reaction mixture $H_2O$, weight ratio 1.3) to the warm oleoresin/propylene glycol mixture.

The saponification reaction mixture was heated to 65° C. and gently agitated for about two hours, maintaining the temperature between 60° C. and 70° C. The saponification reaction caused large, bronze-purple lycopene crystals to form.

Collection Of Lycopene Crystals

After about two hours as described above, the saponification/crystallization reaction mixture was added to 65° C. water (931 g 80 weight percent diluting water and 20 weight percent saponification reaction mixture) to disperse impurities.

To collect the lycopene crystals, the diluted saponification reaction mixture was blended briefly, then poured through a pre-heated filter funnel fitted with a WHATMAN™ No. 4 filter. The filtration step took about 15 minutes. The lycopene crystals were dried by pulling air through the filter for five minutes after the solution was filtered. The collected lycopene crystals weighed 417.5 milligrams.

A portion of the crystals was diluted into hexanes for calorimetric quantitative analysis. The recovered lycopene was 66.7 percent of the total pigment present in the lycopene-containing oleoresin, and 40.8 percent of the total pigment present in the freeze-dried tomato skins. The lycopene crystals did not contain detectable levels of beta-carotene or xanthophylls.

EXAMPLE 2

Isolation Of Lycopene From Dried Tomato Paste

Extraction

A commercially available tomato paste was freeze-dried. Corn oil was added to one-half of the freeze-dried tomato paste to two percent corn oil by weight of that portion of dried tomato paste. Both freeze-dried tomato paste mixtures (with and without corn oil) were separately ground in a WILEY™ mill (Fisher Scientific, Pittsburgh Pa.) fitted with a two millimeter screen and a 30 mesh sieve (0.6 mm). Both powdered mixtures were four-times extracted with one-liter portions of 45° to 50° C. hexanes in 4 L separation funnels for thirty minutes with intermittent swirling. The four extracts were combined in each case. The extraction mixtures were not kept warm during extraction. The ratio of solvent to freeze-dried powder ranged from 0.7 to 0.5 on a weight to weight basis. The combined extracts were separately concentrated on a rotary evaporator, resulting in two lycopene-containing tomato paste oleoresins, one prepared with and one without corn oil.

Saponification/Crystallization Reaction

To each of the lycopene-containing tomato paste oleoresins (6.5 g; 29 weight percent of the final reaction mixture, weight ratio 4.8) was added 1,2-propanediol (13 g; 58 weight percent of the final reaction mixture, weight ratio 9.7). The mixture was heated slightly to 50° C.–80° C. and stirred until it was homogeneous. An aqueous alkaline potash solution containing 45 weight percent potassium hydroxide (2 g of 45 percent caustic potash; 6 weight percent KOH, weight ratio 1; 7 weight percent $H_2O$, weight ratio 1.2) was added to each mixture, and the saponification/crystallization reaction mixture was stirred for thirty minutes at a temperature of about 65° C. The consistency of the blend became less viscous as the saponification reaction proceeded. The saponification reaction induced further lycopene crystal formation.

After thirty minutes, water (100 g; 10–12 μmho; 82 weight percent diluting water and 18 weight percent saponification reaction mixture) at a temperature of about 40° C. to 50° C. was added to each mixture to disperse the saponification reaction products and other impurities. The bronze-purple lycopene crystals were filtered from the saponification/crystallization reaction mixture.

The lycopene crystals (0.14 g) recovered from the lycopene-containing oleoresin from the extraction of the tomato paste with added corn oil were 90 percent pure lycopene, and constituted a 70 percent recovery of the total pigment present in the oleoresin.

The lycopene crystals (0.37 g) recovered from the lycopene-containing oleoresin from the extraction of the tomato paste without added corn oil were 87 percent pure lycopene, and constituted an 88 percent recovery of the total pigment present in the oleoresin.

Analysis of the lycopene crystals gave the following results:

|  | oil | no oil |
|---|---|---|
| Recovered crystal weight (grams) | 0.139 | 0.371 |
| Total carotenoid level (g/kg) | 99.9 | 97.5 |
| Lycopene purity (HPLC adjusted*) | 90.5 | 87.4 |
| Moisture level (water) | <1% | <1% |

*90.6 and 89.6 percents of total carotenoid analyzed as lycopene from the oleoresins prepared with and without added oil, respectively.

Apparently, addition of corn oil during the extraction stage of oleoresin production does not alter the extraction efficiency of lycopene from the tomato paste, but does enhance the extraction of carotenoid pigment other than lycopene.

EXAMPLE 3

Isolation Of Lycopene From Fresh Tomatoes

Extraction

Two preparations of tomato skins were prepared from fresh tomatoes, with and without the seeds. The tomato skin preparations were dried for 24 hours in a forced-air oven at 130° F. The dried skins were ground in a coffee grinder. The tomato skin powder had 5% moisture content. The carotenoid pigment concentration of the samples was 807–820 mg pigment per kg tomato skins for the preparation with seeds and 1027–1044 mg pigment per kg tomato skins for the preparation without seeds. More than 70 percent of the total carotenoid pigment was lycopene according to HPLC analysis of the powders.

The dried tomato skin powders (15 g of each sample) were separately extracted several times with equal weights of hexanes for 1 hour with gentle agitation at 40° C. The carotenoid concentrations of the hexanes extracts were analyzed. The first extract contained between 40 and 50 percent of the extractable carotenoid.

The hexanes extracts were pooled and concentrated using vacuum (25 inches Hg) and heat (45°–50° C.) to produce lycopene-containing oleoresins.

The oleoresin prepared from dried tomato skins with seeds (0.59 g) contained 9.56 grams of carotenoid per kilogram of oleoresin. The amount of the carotenoid from the skins with seeds that was lycopene was 77.2%, according to the relative areas in the HPLC.

The oleoresin prepared from dried tomato skins without seeds (0.28 g) contained 21.31 grams of carotenoid per kilogram of oleoresin. The amount of the carotenoid from the skins without seeds that was lycopene was 83.7%, according to the relative areas in the HPLC.

The starting material without seeds had a higher lycopene extraction efficiency, based on grams carotenoid per gram of oleoresin, especially when the lycopene fraction of the extracted carotenoid is taken into account.

Saponification/Crystallization Reaction

The oleoresin from the tomato skins with and without seeds were combined (0.87 g, 34 weight percent of the final reaction mixture, weight ratio 2), mixed with 1,2-propanediol (0.7 g, 28 weight percent of the final reaction mixture, weight ratio 1.6) and heated to 50° C. An aqueous alkaline potash solution containing 45 weight percent potassium hydroxide (1 g of 45 percent caustic potash: 17 weight percent KOH, weight ratio 1; 21 weight percent KOH, weight ratio 1.2) was added, and the saponification/crystallization reaction mixture was mixed for 30 minutes at 50° C.

The saponification/crystallization reaction mixture was suspended in water (50 mL) and filtered through a sintered glass funnel (25 to 50 μm pore size) to collect the dark purple lycopene precipitate. The precipitated lycopene was washed with water and dried. The precipitated lycopene was about 80 percent pure lycopene by HPLC analysis.

EXAMPLE 4

Effect Of The Treatment Of Freeze-Dried Wet Tomato Skins On The Amount Of Intact Lycopene In The Tomato Source Lycopene Source Wet tomato skins from Siagra Co., Chengmai, Thailand (8.3 kg of the 50 lb batch used in Example 1) were freeze-dried for three days in a tray freeze-dryer (FTS Systems Inc., Stone Ridge N.Y.) to obtain freeze-dried tomato skins (2.08 kg, 24.3 percent moisture) from which five samples were taken.

The first sample of freeze-dried tomato skins was ground in a rotary meat grinder, which separated the seeds from the tomato skins. Further separation using sieves and air separation produced samples that were substantially only from the skins or the seeds of the tomatoes. The skin and seed samples were ground separately in a CYCLOTEC TECATOR™ mill (Fisher Scientific, Pittsburgh Pa.) fitted with a 0.5 mm screen, and found to contain 1328 milligrams of pigment per kilogram of tomato skins and 97 milligrams of pigment per kilogram of tomato seeds. The seeds thus contribute little to the total extractable pigment yet constitute a large portion of the total sample mass.

A second sample was left in flake form, and was dried for 6 days at 30° C. A third sample was ground in a WILEY™ mill (Fisher Scientific, Pittsburgh Pa.) fitted with a 2 mm screen and dried for 6 days at 30° C. A fourth sample was ground in a WILEY™ mill fitted with a 1 mm screen and dried for 6 days at 30° C. A fifth sample was ground in a CYCLOTEC™ mill fitted with a 0.5 mm screen and dried for 6 days at 30° C.

Extraction

At the end of the treatment, all of the samples were extracted with hexanes, analyzed spectrophotometrically, and compared with the amount of lycopene present in the freeze-dried flakes before the 6-day heat treatment. The samples ground in the CYCLOTEC™ mill (<0.5 mm particles) and the WILEY™ mill (<1 mm and <2 mm particles) had more of the oxidized lycopene content than the non-ground (flake) sample: 36, 33, 36 and 25 percent pigment losses, respectively. However, none of the samples after 6 days had over 75 percent of the lycopene that was present before the treatment. The particles of the treated samples exhibited a lightened top crust that extended a short distance into the particle.

EXAMPLE 5

Effect Of Oil And Antioxidant Added To Dried Tomato Skins On The Amount Of Intact Lycopene In The Tomato Source Lycopene Source A lycopene source sample of wet tomato skins from Siagra Co., Chengmai, Thailand (a sample of the 50 lbs used in Examples 1 and 4) was divided into three portions. To the first portion was added canola oil (3.1 percent by weight of the wet tomato skins, 11.6 percent by weight of the dried tomato skins), which was blended into the wet tomato skins in a small KITCHEN AID™ professional blender (Hobart Co., St. Joseph Mo.). To the second portion was added PET-OX™ antioxidant (butylated hydroxyanisole [BHA] and butylated hydroxytoluene [BHT] blend from Kemin Industries, Des Moines Iowa; 286 parts per million [ppm] of the wet tomato skins, 1200 parts per million [ppm] of the dry tomato skins), which was blended into the wet tomato skins in a small HOBART™ mixer. Nothing was added to the third portion, which served as a control.

The three portions of wet tomato skins were dried in a forced-air oven at 120° F. The dried tomato skins were analyzed spectrophotometrically for pigment content after 16 hours and after 40 hours. The pigment content is reported in the table below on a dry weight basis, along with the adjusted percentage of pigment loss relative to the freeze-dried tomato skins before drying in the oven.

|  | Pigment (mg/kg) | Pigment Loss (% loss) |
| --- | --- | --- |
| Freeze-dried skins | 995 | 0.0 |
| 16 hour Control | 902 | 9.3 |
| 16 hour with Antioxidant | 950 | 4.5 |
| 16 hour with Oil | 810 | 9.5 |
| 40 hour Control | 781 | 21.4 |
| 40 hour with Antioxidant | 780 | 24.1 |
| 40 hour with Oil | 653 | 29.7 |

The addition of antioxidant reduced degradation of the lycopene during drying. The addition of oil did not decrease the degradation, but can increase the degradation of the lycopene during extended exposure.

EXAMPLE 6

The Effect Of The Addition Of Oil And Antioxidant On The Extraction Of Lycopene From Tomato Skin Lycopene Source Three samples of wet tomato skins from Siagra Co., Chengmai, Thailand (100 g each from the 50 lb batch of Example 1) were spread onto glass plates and dried at 120° F. in a forced air oven for 19.5 hours. Before drying, corn oil (2 percent by weight of the wet tomato skins) and PET-OX™ antioxidant (1000 ppm BHA/BHT blend from Kemin Industries, Des Moines, Iowa) was added to the first sample. After drying, corn oil (2.25 g) and PET-OX™ antioxidant (1000 ppm BHA/BHT blend from Kemin Industries, Des Moines Iowa) was added to the second sample. Nothing was added to the third control sample. After all three samples were dried, they were ground in a CYCLOTEC 1093™ mill (Fisher Scientific, Pittsburgh Pa.) fitted with a 0.5 mm screen.

Pigment content of the three samples was analyzed by the modified Association of Official Analytical Chemists method (the modification is using hexanes as the final diluent). *Official Methods of Analysis of AOAC International,* 16th Ed., P. Cunniff, ed., AOAC International (Gaithersburg Md.: 1996), March 1996 suppl., sect.45.1.03–04. The pigment in the three samples was also analyzed as follows. The samples (0.5 g) were extracted with hexanes (30 mL, 20 g) at 56° C., resulting in a 40:1 solvent to wet tomato skin weight ratio, then diluted to 100 mL with hexanes. The pigment in the extract was analyzed spectrophotometrically.

The addition of oil enhances the stability of the pigment. There is a slight advantage to the addition of antioxidant to the tomato source prior to extraction.

EXAMPLE 7

Comparison Of Tomato Skins To Tomato Pomace As A Source Of Lycopene

Lycopene Source

Flake dried tomato skins (240° C.) from Siagra Co., Chengmai, Thailand (prepared as described previously from the 50 lbs used in Example 1) and dried, commercially available tomato pomace from LaBudde Feed & Grain Co., Grafton Wis., were compared as tomato sources for carotenoid extracts. The tomato skins from Siagra were treated six different ways as described in the following table. The milled samples were ground in a CYCLOTEC 1093™ mill filled with a 0.5 mm screen. All of the samples were analyzed for carotenoid content using the modified AOAC procedure described above, and analyzed for moisture content.

| Sample Description | Carotenoid (mg/kg) | Moisture (percent) | Spectra (nm) |
| --- | --- | --- | --- |
| Tomato pomace | 239 | 5.3 | 500.5, 469, 444 |
| Siagra, flake dried at 240° C. | 255 | 2.0 | 498.5, 469, 443 |
| Siagra, milled dried at 240° C. | 345 | 1.6 | 497.5, 468, 443 |
| Siagra, twice milled | 1153 | 3.4 | 469.5, 442.5 |
| Siagra dried to 5% moisture* | 469 | 2.9 | 498.5, 469, 443 |
| Siagra dried to 10% moisture | 441 | 5.1 | 499.5, 469.5, 443 |
| Siagra, milled and dried to 14% moisture | 945 | 6.8 | 502, 471, 443.5 |

*Sample too dry to pellet

In each case, the tomato source sample was dark brown, showing oxidation as a result of the harsh drying conditions. The sample that had the highest moisture content (14 percent moisture) had the highest lycopene content and displayed the lycopene spectrum closest to the literature values (maxima at 504–505 nm, 468–472 nm, and 442–444 nm). Liaaen-Jensen, *Phytochemistry,* 4:925–931 (1965); Reichenbach and Kleinig, *Arch. Mikrobiol.,* 76:364–380 (1971).

EXAMPLE 8

Effect Of Acetone On The Extraction Of Lycopene From Tomato Skins

Lycopene Source

Wet tomato skins from Siagra Co., Chengmai, Thailand (59.1 g of the 50 lbs used in Example 1, 76.3 percent moisture) were homogenized (5 minutes) with water (440 g, deionized by reverse osmosis, "RO"). Methanol (400 g) was stirred into the wet homogenate to form a slurry that was allowed to equilibrate (5 minutes) before CELITE™ 545 (diatomaceous silica; 12 g) was added to the slurry. The slurry was then vacuum-filtered through a bed of CELITE™ 545 (diatomaceous silica; 17 g additional, 30 g total) to remove as much water and methanol as possible.

Extraction

The tomato skin solids mixture was suspended in 1:1 (v/v) hexanes:acetone solution (250 mL), stirred for several minutes and filtered. The filtered solid was resuspended and filtered two more times.

The combined hexanes:acetone extracts were poured into a separation funnel (4 L) and washed with a dilute aqueous sodium sulfate solution (10 percent solution), allowing the phases to separate overnight (about 18 hours). The upper organic phase was washed once again with sodium sulfate solution and isolated from the lower aqueous phase containing more polar carotenoids.

The organic phase was dried with anhydrous sodium sulfate and diluted to 1 L with hexanes and analyzed for carotenoid content. The diluted organic phase was evaporated to dryness to produce an oleoresin (1.96 g).

The oleoresin thus formed contained about 1550–1590 mg carotenoid pigment per kg tomato skin extract (oleoresin) on a dry weight basis. HPLC of the oleoresin shows the pigment to be 60 percent lycopene (about 930 mg lycopene per kg oleoresin on a dry weight basis) with the remainder of the pigment being more polar carotenoids. Use of a more polar extractant is effective, but can increase the overall carotenoid yield without substantially increasing lycopene extraction.

EXAMPLE 9

Effect Of Saponification Before Extraction On Carotenoid Extraction Yield

Wet tomato skins from Siagra Co., Chengmai, Thailand (150 g of the 50 lbs used in Example 1 et seq.) were homogenized in a WARING™ blender (Fisher Scientific, Pittsburgh Pa.) with water (450 g, RO) for several minutes. The homogenate was vacuum-filtered through a WHATMAN™ No. 113 filter, and a sample taken (the "wet homogenized tomato skins"). The filtered homogenate pad was pressed to decrease the water content. The homogenate pad was placed on blotter paper and dried at 120° F. for 17 hours in a forced-air oven (the "dried homogenized tomato skins").

The dried homogenized tomato skins contained 836 mg of carotenoid pigment per kg of skins on a dry weight basis. The wet homogenized tomato skins contained 1043 mg of carotenoid per kg of skins on a dry weight basis. The drying degraded the overall carotenoids by about 20 percent.

Wet tomato skins from Siagra Co., Chengmai, Thailand (150 g) were homogenized as described above, except that during filtration, the homogenate was blended with 45 percent potash (10 g) at the temperature of about 50°–80° C. (the saponification reaction is exothermic—heat producing), filtered as described above, and dried at 120° F. for 17 hours in a forced-air oven. The addition of the potash caused an immediate increase in the redness of the homogenate.

The dried homogenized, saponified tomato skins contained 631 mg of carotenoid pigment per kg of skins on a dry weight basis. The wet homogenized, saponified tomato skins contained 800 mg of carotenoid per kg of tomato skins on a dry weight basis. Treatment of the tomato skins with base prior to extraction and oleoresin formation thus leads to decreased carotenoid content in the extract.

EXAMPLE 10

Isolation Of Lycopene Crystals From Yeast Cells That Do Not Normally Produce Lycopene Normal yeast cells do not produce lycopene. Lycopene production capability is conferred on yeast by introducing the biological activity of three enzymes, geranylgeranyl pyrophosphate (GGPP) synthase, phytoene synthase and phytoene dehydrogenase-4H, as described in U.S. Pat. No. 5,530,189.

Briefly, plasmids harboring genes encoding GGPP synthase, phytoene synthase and phytoene dehydrogenase-4H are transformed into the yeast *Saccharomyces cerevisiae*, strain YPH499. Plasmids used to transform the yeast cells are constructed as described in U.S. Pat. No. 5,530,189 and briefly summarized below.

Genes that encode biologically active versions of GGPP synthase and phytoene synthase are ligated into a plasmid expression vector such as vector pSOC925 such that GGPP synthase expression is under the control of the GAL 10 promoter and phytoene synthase expression is under the control of the divergent GAL 1 promoter. The resulting plasmid pARC145G was deposited with the American Type Culture Collection (ATCC) as accession No. 40753.

A gene that encodes a biologically active version of the phytoene dehydrogenase-4H gene is ligated into another expression vector such as modified plasmid expression vector pSOC713 such that phytoene dehydrogenase-4H expression is under the control of the GAL 1 promoter and the PGK terminator. The resulting plasmid pARC146D has ATCC accession number 40801.

The yeast strain YPH499 contains a non-functional tryptophan biosynthesis gene (TRP 1) and a non-functional uracil biosynthesis gene (URA 3). Plasmid pARC145G contains a functioning TRP 1 gene as well as the genes for GGPP synthase and phytoene synthase. Plasmid pARC146D contains a functioning URA 3 gene as well as the gene for phytoene dehydrogenase-4H. Both plasmids are transformed into the yeast YPH499 cells, and the double-transformants are selected by the following uracil- and tryptophan-deficient medium: 0.67% yeast nitrogen base without amino acids (0.67% Difco #0919-15); 2% galactose; 0.72% essential nutrient mixture. The essential nutrient mixture contains the following, ground thoroughly together with a mortar and pestle: adenine (400 mg); histidine (400 mg); arginine (400 mg); methionine (400 mg); tyrosine (600 mg); leucine (1200 mg); lysine (600 mg); phenylalanine (1000 mg); threonine (4000 mg); and aspartic acid (2000 mg).

Galactose is added to induce the expression of the lycopene-producing genes. The cells are grown to stationary phase, and are collected by centrifugation to form a pellet followed by decantation of the growth medium. Yeast cells with the three genes produced lycopene at about 0.01 percent dry weight, according to U.S. Pat. No. 5,530,189.

Extraction

The collected cells are dried, lysed and extracted with hexanes. The hexanes extract is washed with water, and then the solvent is removed by evaporation under reduced pressure, leaving a lycopene-containing yeast oleoresin.

Saponification/Crystallization Reaction

Propylene glycol is added to the lycopene-containing oleoresin such that the weight ratio of propylene glycol to oleoresin is 3:5. The mixture is warmed to 55° C. with agitation.

An aqueous alkaline potash solution containing 45 weight percent potassium hydroxide (2:5 weight ratio of potash solution to oleoresin) is blended into the warm oleoresin mixture. The saponification/crystallization reaction mixture thus formed (about 5:3:1:1 oleoresin to propylene glycol to alkali to water) is stirred for an hour maintaining the temperature between 55° C. and 70° C.

Collection Of The Lycopene Crystals

Warm water (60° C. to 70° C.) is stirred into the saponification/crystallization reaction mixture in a ratio of about 8 volumes of water per reaction mixture volume. The resulting solution is filtered to isolate the lycopene crystals. The lycopene crystals are washed with more warm water and dried under a stream of warm nitrogen.

EXAMPLE 11

Isolation Of Lycopene Crystals From Plant Cells That Do Not Normally Accumulate Lycopene Lycopene Source Higher plants usually have the ability to produce lycopene, but the lycopene is often further converted to other products and does not accumulate. Even in the case of ripe tomatoes, accumulated lycopene is about 0.01 percent dry weight. The lycopene accumulation in tobacco plants is improved by the introduction of a gene encoding phytoene dehydrogenase-4H, as described in U.S. Pat. No. 5,530,189. Briefly, the gene is introduced into *Agrobacterium tumefaciens*, which is used to infect tobacco.

Plasmid pATC1616, ATCC accession No. 40806, is a plasmid vector harboring a gene encoding a biologically active phytoene dehydrogenase-4H protein. The plasmid also has (i) an origin of replication that permits maintenance of the plasmid in *Agrobacterium tumefaciens*, (ii) the left and right border sequences from the T-DNA region that direct the integration of the phytoene dehydrogenase-4H DNA segment between the borders into the plant genome, and (iii) the NOS promoter adjacent to the kanamycin resistance gene that permits plant cells to survive in the presence of kanamycin.

Plasmid pATC1616 is transformed into *Agrobacterium tumefaciens* strain LBA4404 (Clontech, Inc.) according to standard protocols. Transgenic tobacco plants are generated by infecting tobacco leaf discs with the transformed agrobacteria using the method of Horsch et al., *Science*, 227:1229–1231 (1985).

The transgenic tobacco plants are grown in the presence of an amount of the herbicide norflurazon (Sandoz; 0.8 micrograms per milliliter) that plants not containing the plasmid phytoene dehydrogenase-4H could not withstand. Lycopene is produced in the chloroplasts of the plant causing the plant to turn red.

Extraction

The transgenic tobacco plants are harvested. The tobacco leaves are homogenized in a blender. One volume of hexanes is blended into the homogenate for an hour, then filtered off. The aqueous phase is permitted to separate and is drained off. This step is repeated with one-half volume of hexanes. The lycopene-containing hexanes extracts are washed with water and combined. The organic solvent is removed from the formed lycopene-containing oleoresin by rotary evaporation at reduced pressure in a warm water bath to form a lycopene-containing plant oleoresin.

Saponification/Crystallization Reaction

Equal weights of 1,2-propanediol and lycopene-containing oleoresin are admixed. One-fourth weight (relative to the oleoresin) of an aqueous alkaline potash solution comprising 45 percent potassium hydroxide is blended into the mixture. The saponification/crystallization reaction mixture is blended at a temperature of 55° C. to 65° C. for an hour.

Collection Of The Lycopene Crystals

After an hour, seven volumes of warm water is mixed into the saponification/crystallization reaction mixture. The lycopene crystals are collected by vacuum filtration, and washed with warm water.

EXAMPLE 12

Isolation Of Lycopene Crystals From Fungi That Do Not Normally Accumulate Lycopene Lycopene Source Genes encoding GGPP synthase, phytoene synthase, and phytoene dehydrogenase-4H are transferred into *Aspergillus nidulans* as described in U.S. Pat. No. 5,530,189 using techniques well-known in the art.

Briefly, the structural gene for GGPP synthase, the amds gene [Corrick et al., *Gene*, 53:63–71 (1987)], and the Aspergillus promoter argB [Upshall et al., *Mol. Gen. Genet.*, 204:349–354 (1986)], are introduced into the commercially available plasmid pBR322 (United States Biochemical Corp., Cleveland Ohio) such that the GGPP synthase gene is under the control of the argB promoter, and plasmid-containing Aspergillus cells are selectable by growth in media where acetamide is the sole carbon or nitrogen source.

The structural genes for phytoene synthase and phytoene dehydrogenase-4H, the Aspergillus trpC gene [Hamer and Timberlake, *Mol. Cell. Biol.*, 7:2352–2359 (1987)], and the Aspergillus promoter argb, are introduced into the plasmid pBR322 such that the phytoene synthase and phytoene dehydrogenase-4H genes are under the control of the argB promoter, and plasmid-containing Aspergillus cells are selectable by growth in media lacking tryptophan.

The plasmids are transferred to *Aspergillus nidulans* cells by the integration method of Ballance et al., *Biochem. Biophys. Res. Commun.*, 112:284–289 (1983). The cells containing stable plasmids are selected as described above. These fungal cells accumulate lycopene.

The lycopene-accumulating cells are grown on Aspergillus medium (1.0 g yeast extract, 1.0 g peptone, 6.0 g $NaNO_3$, 1.0 g casamino acids, 15.0 g agar, and 0.15 g adenine per liter of distilled water) containing a vitamin solution (10 mL; 0.01 g each of biotin, pyridoxine HCl, thiamine HCl, riboflavin, p-aminobenzoic acid, and nicotinic acid per 100 mL distilled water). The fungi are harvested after a stationary phase is reached.

Extraction

A hexanes extract is formed from the lycopene-containing fungal cells. The solvent is removed from the hexanes extract by rotary evaporation under reduced pressure to form a lycopene-containing oleoresin.

Saponification/Crystallization Reaction

An equal weight of propylene glycol is added to the lycopene-containing oleoresin, mixed and warmed to a temperature of about 60° C. One-fourth weight (relative to the oleoresin) of an aqueous alkali solution containing 45 weight percent potassium hydroxide is added. The saponification/crystallization reaction mixture is stirred and maintained between 55° C. and 65° C. for an hour.

Collection Of The Lycopene Crystals

The saponification/crystallization reaction mixture is diluted with four volumes of warm water (75° C.) then filtered to cool the lycopene crystals. The lycopene crystals are washed with warm water and freeze-dried.

EXAMPLE 13

Isolation Of Lycopene Crystals From Bacteria That Do Not Normally Produce Lycopene Lycopene Source Ubiquitous cellular precursors can be converted into lycopene by the combined action of GGPP synthase, phytoene synthase and phytoene dehydrogenase-4H. Lycopene is produced in *Escherichia coli* by introducing plasmids containing the three genes for the above enzymes as described in U.S. Pat. No. 5,530,189.

Briefly, the GGPP synthase and phytoene synthase genes from *Erwinia herbicola* plasmid pARC376 [Perry et al., *J. Bacteriol.*, 168:607 (1986)] are cloned into the plasmid pSOC925, containing genes for kanamycin resistance, forming the plasmid pARC275. The plasmid pARC275 is transformed into *E. coli* HB101 cells grown in Luria broth in the presence of 25 micrograms kanamycin per milliliter. As a result, the pARC275 transformants accumulate phytoene, a biological lycopene precursor.

The plasmid pARC496A (ATCC accession No. 40803) contains the structural gene for phytoene dehydrogenase-4H and the genes for ampicillin resistance. The plasmid pARC496A is transformed into *E. coli* HB101 cells harboring the pARC275 plasmid. The double-transformants are selected by growing the host cell in medium supplement with 25 micrograms kanamycin and 100 micrograms ampicillin per milliliter media.

Extraction

The reportedly red double-transformants are harvested when stationary phase is reached. The lycopene containing *E. coli* cells are lysed and extracted with hexanes to form an oleoresin.

Saponification/Crystallization Reaction

An equal weight of propylene glycol is added to the lycopene-containing oleoresin, mixed and warmed to a temperature of 60° C. One-fourth weight (relative to the oleoresin) of an aqueous alkali solution comprising 45 weight percent potassium hydroxide is added. The saponification/crystallization reaction mixture is stirred and maintained between 55° C. and 65° C. for an hour.

Collection Of The Lycopene Crystals

The saponification/crystallization reaction mixture is diluted with four volumes of warm water (75° C.) then filtered to cool the lycopene crystals. The lycopene crystals are washed with warm water and freeze-dried.

The foregoing description and the examples are intended as illustrative and are not to be taken as limiting. Still other variations within the spirit and scope of this invention are possible and will readily present themselves to those skilled in the art.

We claim:

1. A process for producing lycopene crystals from a lycopene-containing oleoresin, said oleoresin also comprising cellular debris, said process comprising the steps of:
   (a) admixing said oleoresin with propylene glycol, alkali and water to form a saponification reaction mixture;
   (b) maintaining said saponification reaction mixture at a temperature of about 50° C. to about 80° C. for a time period sufficient to saponify the cellular debris and form a saponified reaction mixture containing lycopene crystals;
   (c) admixing one volume of said saponified reaction mixture with about 3 to about 19 volumes of water at a temperature of about 40° C. to about 80° C. to form a diluted reaction mixture containing lycopene crystals; and
   (d) collecting the lycopene crystals from said diluted reaction mixture.

2. The process of claim 1 wherein said oleoresin is prepared from bacterial cells.

3. The process of claim 1 wherein said oleoresin is prepared from yeast or fungal cells.

4. The process of claim 1 wherein said oleoresin is prepared from plant cells.

5. The process of claim 4 wherein said plant cells are from tomatoes.

6. The process of claim 1 wherein step (a) comprises the following steps:
   (i) admixing said oleoresin with said propylene glycol with heating to a temperature of about 50° C. to about 60° C. to form a homogeneous liquid; and
   (ii) admixing an aqueous alkali solution of said alkali and water with said homogeneous liquid to form a saponification reaction mixture.

7. The process of claim 1 wherein said saponification reaction mixture comprises about 25 to about 50 weight percent oleoresin, about 25 to about 60 weight percent propylene glycol, about 5 to about 20 weight percent alkali and about 5 to about 25 weight percent water as initially admixed components, wherein the total weight of said oleoresin plus propylene glycol constitute at least about 50 weight percent of said reaction mixture.

8. The process of claim 1 wherein the saponification reaction mixture is maintained for a time period of at least 0.5 hours.

9. The process of claim 1 including the further step:
   (e) admixing said dried lycopene crystals with a triglyceride oil to form a lycopene crystal suspension or solution comprising an admixture containing about 0.1 to about 35 weight percent lycopene.

10. A process for producing a lycopene crystal suspension or solution from a lycopene-containing oleoresin, said oleoresin also comprising cellular debris, said process comprising the steps of:
    (a) admixing said lycopene-containing oleoresin with propylene glycol, alkali and water to form a saponification reaction mixture that comprises about 25 to about 50 weight percent oleoresin, about 25 to about 60 weight percent propylene glycol, about 5 to about 20 weight percent alkali and about 5 to about 25 weight percent water as initially admixed components, wherein the total weight of said oleoresin plus propylene glycol constitute at least about 50 weight percent of said saponification reaction mixture;
    (b) maintaining said saponification reaction mixture at a temperature of about 50° C. to about 80° C. for a time period sufficient to saponify the cellular debris and form a saponified reaction mixture containing lycopene crystals;
    (c) admixing one volume of said saponified reaction mixture with about 3 to about 19 volumes of water at a temperature of about 40° C. to about 80° C. to form a diluted reaction mixture containing lycopene crystals;
    (d) collecting the lycopene crystals from said diluted reaction mixture; and
    (e) admixing said dried lycopene crystals with a triglyceride oil to form a lycopene crystal suspension or solution comprising an admixture containing about 0.1 to about 35 weight percent lycopene.

11. The process of claim 10 wherein said oleoresin is prepared from bacterial cells.

12. The process of claim 10 wherein said oleoresin is prepared from yeast or fungal cells.

13. The process of claim 10 wherein said oleoresin is prepared from plant cells.

14. The process of claim 13 wherein said plant cells are from tomato.

15. The process of claim 14 wherein said tomato is in the form of tomato skins.

16. The process of claim 14 wherein said tomato is in the form of tomato paste.

17. The process of claim 14 wherein said tomato is in the form of tomato pomace.

18. The process of claim 10 wherein said alkali is potassium hydroxide.

19. The process of claim 10 wherein said step (a) comprises the following steps:
    (i) admixing said oleoresin with said propylene glycol with heating to a temperature of about 50° C. to about 60° C. to form a homogeneous liquid; and
    (ii) admixing an aqueous alkali solution of said alkali and water with said homogeneous liquid to form a saponification reaction mixture.

* * * * *